(12) United States Patent
Dunkel et al.

(10) Patent No.: US 8,580,971 B2
(45) Date of Patent: Nov. 12, 2013

(54) ALKYL-ANALIDE PRODUCING METHOD

(75) Inventors: Ralf Dunkel, Lyons (FR); Hans-Ludwig Elbe, Wuppertal (DE); Jörg Nico Greul, Leichlingen (DE); Herbert Gayer, Monheim (DE); Thomas Seitz, Langenfeld (DE); Peter Dahmen, Neuss (DE); Ulrike Wachendorff-Neumann, Neuwied (DE)

(73) Assignee: Bayer CropScience AG, Monheim (DE)

( * ) Notice: Subject to any disclaimer, the term of this patent is extended or adjusted under 35 U.S.C. 154(b) by 701 days.

(21) Appl. No.: 11/817,434

(22) PCT Filed: Feb. 21, 2006

(86) PCT No.: PCT/EP2006/001520
§ 371 (c)(1),
(2), (4) Date: May 14, 2008

(87) PCT Pub. No.: WO2006/092213
PCT Pub. Date: Sep. 8, 2006

(65) Prior Publication Data
US 2009/0118346 A1    May 7, 2009

(30) Foreign Application Priority Data
Mar. 2, 2005  (DE) .......................... 10 2005 009 458

(51) Int. Cl.
*C07D 231/00* (2006.01)

(52) U.S. Cl.
USPC ...................................................... 548/374.1

(58) Field of Classification Search
USPC ...................................................... 548/374.1
See application file for complete search history.

(56) References Cited

U.S. PATENT DOCUMENTS

| | | | |
|---|---|---|---|
| 5,093,347 A | 3/1992 | Graneto et al. | |
| 5,330,995 A | 7/1994 | Eicken et al. | |
| 5,914,344 A | 6/1999 | Yoshikawa et al. | |
| 5,998,450 A | 12/1999 | Eicken et al. | |
| 7,329,633 B2 | 2/2008 | Dunkel et al. | |
| 7,358,214 B2 | 4/2008 | Dunkel et al. | |
| 7,521,397 B2 | 4/2009 | Dunkel et al. | |
| 7,538,073 B2 | 5/2009 | Elbe et al. | |
| 7,799,739 B2 | 9/2010 | Dunkel et al. | |
| 7,820,708 B2 | 10/2010 | Dunkel et al. | |
| 7,879,760 B2 | 2/2011 | Dunkel et al. | |
| 2007/0060579 A1 | 3/2007 | Wachendorff-Neumann et al. | |
| 2007/0196406 A1 | 8/2007 | Dunkel et al. | |
| 2008/0255071 A1 | 10/2008 | Suty-Heinze et al. | |
| 2009/0069398 A1 | 3/2009 | Dunkel et al. | |
| 2009/0105311 A1 | 4/2009 | Dunkel et al. | |
| 2009/0118346 A1 | 5/2009 | Dunkel et al. | |
| 2009/0286681 A1 | 11/2009 | Dahmen et al. | |
| 2011/0105331 A1 | 5/2011 | Ebbinghaus et al. | |

FOREIGN PATENT DOCUMENTS

| | | | |
|---|---|---|---|
| EP | 0 545 099 A1 | 6/1993 | |
| JP | 01-290662 | 11/1989 | |
| JP | 09-132567 | 5/1997 | |
| WO | WO 97/08148 A1 | 3/1997 | |
| WO | WO 03/070705 | * 8/2003 | ........... C07D 321/14 |
| WO | WO 2006/037632 A1 | 4/2006 | |

OTHER PUBLICATIONS

English Translation of the Written Opinion of the International Searching Authority for International Application No. PCT/EP2006/001520, European Patent Office, Netherlands, mailed on Sep. 2, 2007.

Patent Abstracts of Japan, English-language abstract for JP 01-290662 (listed on accompanying PTO/SB/08a as document FP3), accessed on Oct. 28, 2009.

Patent Abstracts of Japan, English-language abstract for JP 09-132567 (listed on accompanying PTO/SB/08a as document FP4), accessed on Oct. 28, 2009.

Kosack, J.R., Office Action for U.S. Appl. No. 10/504,451: inventors: Dunkel et al., U.S. Patent and Trademark Office, Alexandria, Virginia, mailed May 30, 2007.

Kosack, J.R., Office Action for U.S. Appl. No. 10/504,451: inventors: Dunkel et al., U.S. Patent and Trademark Office, Alexandria, Virginia, mailed Mar. 27, 2007.

Kosack, J.R., Office Action for U.S. Appl. No. 10/504,451: inventors: Dunkel et al., U.S. Patent and Trademark Office, Alexandria, Virginia, mailed Oct. 3, 2006.

Office Action dated Jul. 18, 2011, in U.S. Appl. No. 11/916,436, Dunkel, R. et al., filed Nov. 7, 2008.

(Continued)

*Primary Examiner* — Paul Zarek
(74) *Attorney, Agent, or Firm* — Sterne, Kessler, Goldstein & Fox P.L.L.C.

(57) ABSTRACT

New pyrazolylcarboxanilides of the formula (I)

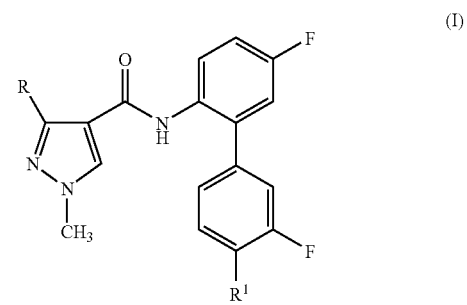

in which R and $R^1$ have the meanings given in the description, a plurality of processes for the preparation of these substances and their use for controlling undesired microorganisms, and novel intermediates and their preparation.

14 Claims, No Drawings

(56) References Cited

OTHER PUBLICATIONS

Office Action dated Jan 30, 2012, in U.S. Appl. No. 11/916,436, Dunkel, R. et al., filed Nov. 7, 2008.

Patani, G.A. and Lavoie, E.J., "Biosterioism: A Rational Approach in Drug Design," *Chem. Rev.* 69(8):3147-3176, American Chemical Society, United States (1996).

* cited by examiner

ALKYL-ANALIDE PRODUCING METHOD

This application is a National Stage of International Application No. PCT/EP2006/001520 filed Feb. 21, 2006, which claims the benefit of DE 102005009458.9, filed Mar. 2, 2005. The entirety of each of these applications is incorporated by reference herein.

The present invention relates to new pyrazolylcarboxanilides, to a plurality of processes for their preparation and their use for controlling harmful microorganisms in plant protection and in the protection of materials.

It has already been disclosed that a large number of carboxanilides have fungicidal properties (cf., for example, WO 03/070705, EP 0 545 099 and JP 9132567). While the activity of the substances described therein is good, it sometimes leaves something to be desired when low application rates are used.

There have now been found new pyrazolylcarboxanilides of the formula (I)

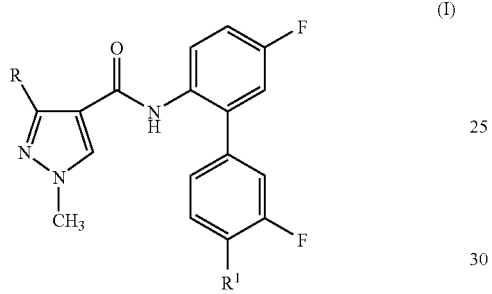

in which
R represents difluoromethyl or trifluoromethyl and
$R^1$ represents chlorine or methyl.

It has furthermore been found that pyrazolylcarboxanilides of the formula (I) are obtained by a) reacting pyrazolylcarboxylic acid halides of the formula (II)

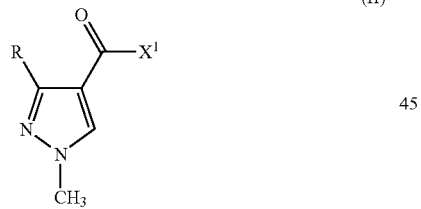

in which
R has the abovementioned meanings and
$X^2$ represents halogen
with aniline derivatives of the formula (III)

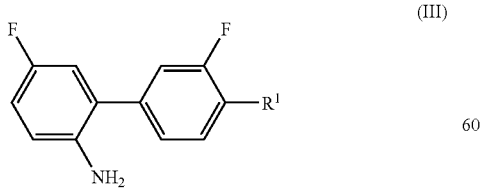

in which $R^1$ has the abovementioned meanings,
if appropriate in the presence of an acid binder and if appropriate in the presence of a diluent, or b) reacting halopyrazolylcarboxanilides of the formula (IV)

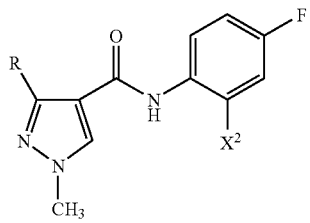

in which
R has the abovementioned meanings and
$X^2$ represents bromine or iodine
with boronic acid derivatives of the formula (V)

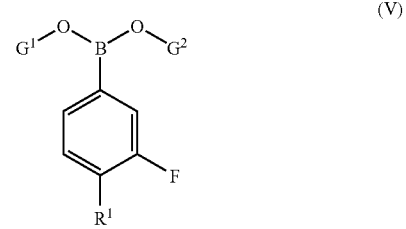

in which
$R^1$ has the abovementioned meanings and
$G^1$ and $G^2$ represent in each case hydrogen or together represent tetramethylethylene
in the presence of a catalyst, if appropriate in the presence of an acid binder and if appropriate in the presence of a diluent, or c) reacting halopyrazolylcarboxanilides of the formula (IV)

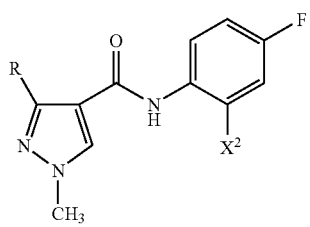

in which
R has the abovementioned meanings and
$X^2$ represents bromine or iodine
in a first step with a diborane derivative of the formula (VI)

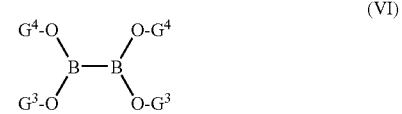

in which
$G^3$ and $G^4$ represent in each case alkyl or together represent alkanediyl
in the presence of a catalyst, if appropriate in the presence of an acid binder and if appropriate in the presence of a diluent and, without work-up, in a second step with halobenzene derivatives of the formula (VII)

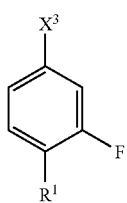

(VII)

in which
R¹ has the abovementioned meanings and
X³ represents bromine, iodine or trifluoromethylsulphonyloxy
in the presence of a catalyst, if appropriate in the presence of an acid binder and if appropriate in the presence of a diluent.

Finally, it has been found that the new pyrazolylcarboxanilides of the formula (I) have very good microbicidal properties and can be used for controlling undesired microorganisms in crop protection and also in the protection of materials.

Surprisingly, the inventive pyrazolylcarboxanilides of the formula (I) have a considerably better fungicidal activity than the prior-art active compounds of the same direction of action which are most similar in terms of constitution.

Formula (I) provides a general definition of the pyrazolylcarboxanilides according to the invention. Formula (I) embraces the following four pyrazolylcarboxanilides:
N-(4'-chloro-3',5-difluorobiphenyl-2-yl)-3-(difluoromethyl)-1-methyl-1H-pyrazole-4-carboxamide
N-(4'-chloro-3',5-difluorobiphenyl-2-yl)-1-methyl-3-(trifluoromethyl)-1H-pyrazole-4-carboxamide
N-(3',5-difluoro-4'-methylbiphenyl-2-yl)-1-methyl-3-(difluoromethyl)-1H-pyrazole-4-carboxamide
N-(3',5-difluoro-4'-methylbiphenyl-2-yl)-1-methyl-3-(trifluoromethyl)-1H-pyrazole-4-carboxamide If, for example, 1-methyl-3-(trifluoromethyl)-1H-pyrazole-4-carbonyl chloride and 4'-chloro-3',5-difluoro-1,1'-biphenyl-2-amine as starting materials plus a base are used, the course of process a) according to the invention can be illustrated by the following equation:

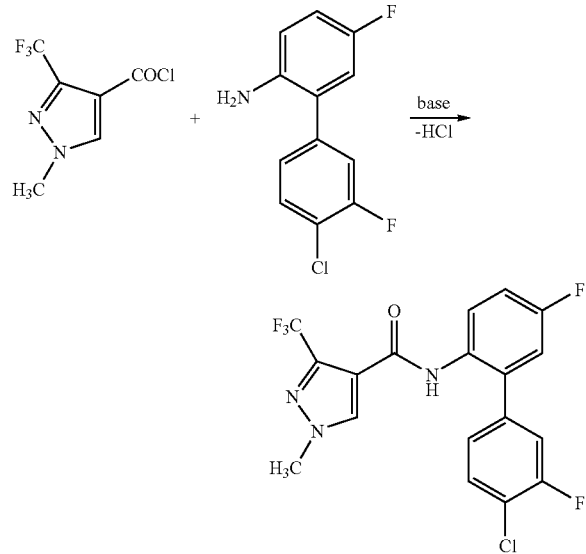

Formula (II) provides a general definition of the pyrazolylcarboxylic acid halides required as starting materials for carrying out process a) according to the invention. In this formula (II), R represents difluoromethyl or trifluoromethyl. X¹ preferably represents chlorine.

The pyrazolylcarboxylic acid halides of the formula (II) are known and/or can be prepared by known processes (cf., for example, JP 01290662 and U.S. Pat. No. 5,093,347).

Formula (III) provides a general definition of the aniline derivatives furthermore required as starting materials for carrying out process a) according to the invention. In this formula (III), R¹ represents chlorine or methyl.

The aniline derivatives of the formula (III) are known and/or can be prepared by known processes (cf. WO 03/070705).

If N-(2-bromo-4-fluorophenyl)-1-methyl-3-(trifluoromethyl)-1H-pyrazole-4-carboxamide and 4-chloro-3-fluorophenylboronic acid as starting materials plus a catalyst and a base are used, the course of process b) according to the invention can be illustrated by the following equation:

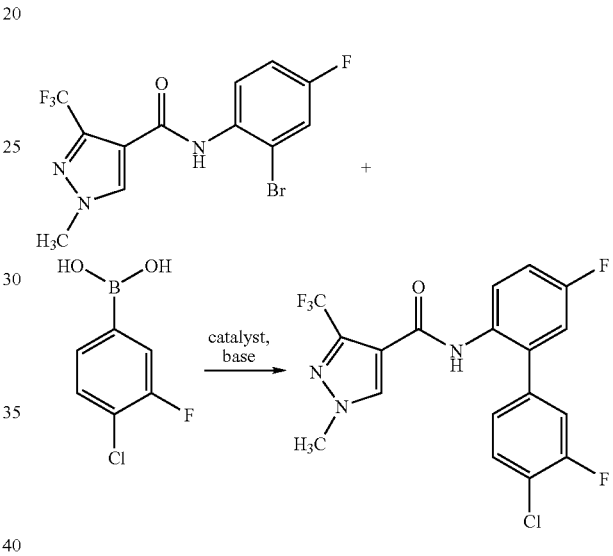

Formula (IV) provides a general definition of the halogenpyrazolylcarboxanilides required as starting materials for carrying out process b) according to the invention. In this formula (IV), R represents difluoromethyl or trifluoromethyl. X² preferably represents bromine or iodine.

The halopyrazolylcarboxanilides of the formula (IV) are known (cf. WO 03/070705).

Formula (V) provides a general definition of the boronic acid derivatives furthermore required as starting materials for carrying out process b) according to the invention. In this formula (V), R¹ represents chlorine or methyl. G¹ and G² preferably represent in each case hydrogen or together represent tetramethylethylene.

Boronic acids of the formula (V) are known chemicals for synthesis. They can also be prepared directly from halobenzene derivatives and boronic esters, immediately before the reaction, and further reacted without work-up.

If, for example, N-(2-bromo-4-fluorophenyl)-1-methyl-3-(trifluoromethyl)-1H-pyrazole-4-carboxamide and 4,4,4',4',5,5,5',5'-octamethyl-2,2'-bi-1,3,2-dioxaborolane are used as starting materials in the first step and furthermore 5-bromo-2-chloro-1-fluorobenzene as starting materials in the second step, plus in each step a catalyst and a base, the course of process c) according to the invention can be illustrated by the following equation:

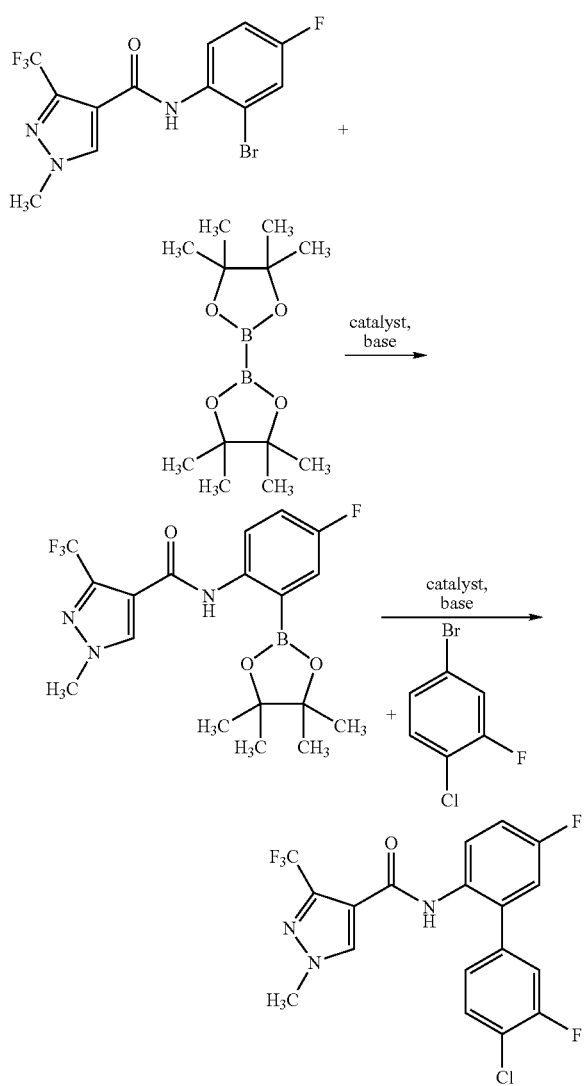

The halopyrazolylcarboxanilides of the formula (IV) which are required as starting materials for carrying out process c) according to the invention have already been described further above in connection with process b) according to the invention.

Formula (VI) provides a general definition of the diborane derivatives furthermore required as starting materials for carrying out process c) according to the invention. In this formula (VI), $G^3$ and $G^4$ preferably represent in each case methyl, ethyl, propyl, butyl, or together represent tetramethylethylene.

The diborane derivatives of the formula (VI) are generally known chemicals for synthesis.

Formula (VII) provides a general definition of the halobenzene derivatives furthermore required as starting materials for carrying out process c) according to the invention. In this formula (VII), $R^1$ represents chlorine or methyl. $X^3$ preferably represents bromine, iodine or trifluoromethylsulphonyloxy.

The halobenzene derivatives of the formula (VII) are generally known chemicals for synthesis.

Diluents which are suitable for carrying out process a) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole or amides, such as N,N-dimethylformamide, N,N-dimethylacetamide, N-methylformanilide, N-methylpyrrolidone or hexamethylphosphoric triamide.

If appropriate, process a) according to the invention is carried out in the presence of a suitable acid acceptor. Suitable acid acceptors are all customary inorganic or organic bases. These preferably include the hydrides, hydroxides, amines, alkoxides, acetates, carbonates or hydrogen carbonates of alkaline earth metals or alkali metals, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or caesium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process a) according to the invention, the reaction temperatures can be varied within a substantial range. In general, the process is carried out at temperatures of from 0° C. to 150° C., preferably at temperatures of from 20° C. to 1110° C.

To carry out process a) according to the invention for the preparation of the compounds of the formula (I), 0.2 to 5 mols, preferably 0.5 to 2 mols of aniline derivative of the formula (III) are generally employed per mole of the pyrazolylcarboxylic acid halide of the formula (II).

Diluents for carrying out processes b) and c) are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, s- or t-butanol, ethanediol, propane-1,2-diol, ethoxyethanol, methoxyethanol, diethylene glycol monomethyl ether, diethylene glycol monoethyl ether, their mixtures with water, or pure water.

When carrying out process b) and c) according to the invention, the reaction temperatures can be varied within a substantial range. In general, the process is carried out at temperatures of from 0° C. to 150° C., preferably at temperatures of from 20° C. to 110° C.

If appropriate, processes b) and c) according to the invention are carried out in the presence of a suitable acid acceptor. Suitable acid acceptors are all customary inorganic or organic bases. These preferably include the hydrides, hydroxides, amides, alkoxides, acetates, fluorides, phosphates, carbonates or hydrogen carbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, potassium acetate, sodium phosphate, potassium phosphate, potassium fluoride, caesium fluoride, sodium carbonate, potassium carbonate, potassium hydrogen carbonate, sodium hydrogen carbonate or caesium carbonate, other tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Processes b) and c) according to the invention are carried out in the presence of a catalyst such as, for example, a palladium salt or palladium complex. Suitable for this purpose are preferably palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture when a palladium salt and a complex ligand such as, for example, triethylphosphane, tri-tert-butylphosphane, tricyclohexylphosphane, 2-(dicyclohexylphosphane) biphenyl, 2-(di-tert-butylphosphane)biphenyl, 2-(dicyclohexylphosphane)-2'-(N,N-dimethylamino)biphenyl, triphenylphosphane, tris-(o-tolyl)phosphane, sodium 3-(diphenylphosphino)benzenesulphonate, tris-2-(methoxyphenyl)phosphane, 2,2'-bis-(diphenylphosphane)-1,1'-binaphthyl, 1,4-bis(diphenylphosphane)butane, 1,2-bis-(diphenylphosphane)ethane, 1,4-bis(dicyclohexylphosphane)butane, 1,2-bis-(dicyclohexylphosphane)ethane, 2-(dicyclohexylphosphane)-2'-(N,N-dimethylamino)biphenyl, bis(diphenylphosphino)ferrocene or tris-(2,4-tert-butylphenyl) phosphite are added separately to the reaction.

For carrying out process b) according to the invention for the preparation of the compounds of the formula (I), 1 to 15 mols, preferably 1 to 5 mols, of boronic acid derivative of the formula (V) are generally employed per mole of the halopyrazolylcarboxanilide of the formula (IV).

For carrying out process c) according to the invention for the preparation of the compounds of the formula (I), 1 to 15 mols, preferably 1 to 5 mols, of diborane derivative of the formula (VI) and 1 to 15 mols, preferably 1 to 5 mols, of halobenzene derivative of the formula (VII) are generally employed per mole of the halopyrazolylcarboxanilide of the formula (IV).

Processes a), b) and c) according to the invention are generally carried out under atmospheric pressure. However, it is also possible to carry out the processes under elevated or reduced pressure, in general between 0.1 bar and 10 bar.

The substances according to the invention exhibit a potent microbicidal activity and can be employed in plant protection and in the protection of materials for controlling undesirable microorganisms such as fungi and bacteria.

Fungicides can be employed in plant protection for controlling Plasmodiophoromycetes, Oomycetes, Chytridiomycetes, Zygomycetes, Ascomycetes, Basidiomycetes and Deuteromycetes.

Bactericides can be employed in plant protection for combating Pseudomonadaceae, Rhizobiaceae, Enterobacteriaceae, Corynebacteriaceae and Streptomycetaceae.

Examples which may be mentioned, but not by limitation, of some pathogens of fungal and bacterial diseases which come under the abovementioned general terms are:

Diseases caused by powdery mildew pathogens, such as, for example
Blumeria species such as, for example, *Blumeria graminis*;
Podosphaera species such as, for example, *Podosphaera leucotricha*;
Sphaerotheca species such as, for example, *Sphaerotheca fuliginea*;
Uncinula species such as, for example, *Uncinula necator*;
Diseases caused by rust pathogens such as, for example,
Gymnosporangium species such as, for example, *Gymnosporangium sabinae*
Hemileia species such as, for example, *Hemileia vastatrix*;
Phakopsora species such as, for example, *Phakopsora pachyrhizi* and *Phakopsora meibomiae*;
Puccinia species such as, for example, *Puccinia recondita*;
Uromyces species such as, for example, *Uromyces appendiculatus*;
Diseases caused by pathogens from the Oomycetene group such as, for example,
Bremia species such as, for example, *Bremia lactucae*;
Peronospora species such as, for example, *Peronospora pisi* or *P. brassicae*;
Phytophthora species such as, for example, *Phytophthora infestans*;
Plasmopara species such as, for example, *Plasmopara viticola*;
Pseudoperonospora species such as, for example, *Pseudoperonospora humuli* or *Pseudoperonospora cubensis*;
Pythium species such as, for example, *Pythium ultimum*;
Leaf spot diseases and leaf wilts caused by, for example,
Alternaria species such as, for example, *Alternaria solani*;
Cercospora species such as, for example, *Cercospora beticola*;
Cladiosporum species such as, for example, *Cladiosporium cucumerinum*;
Cochliobolus species such as, for example, *Cochliobolus sativus*
(conidial form: *Drechslera*, syn: *Helminthosporium*);
Colletotrichum species such as, for example, *Colletotrichum lindemuthianum*;
Cycloconium species such as, for example, *Cycloconium oleaginum*;
Diaporthe species such as, for example, *Diaporthe citri*;
Elsinoe species such as, for example, *Elsinoe fawcettii*;
Gloeosporium species such as, for example, *Gloeosporium laeticolor*;
Glomerella species such as, for example, *Glomerella cingulata*;
Guignardia species such as, for example, *Guignardia bidwelli*;
Leptosphaeria species such as, for example, *Leptosphaeria maculans*;
Magnaporthe species such as, for example, *Magnaporthe grisea*;
Mycosphaerella species such as, for example, *Mycosphaerelle graminicola*;
Phaeosphaeria species such as, for example, *Phaeosphaeria nodorum*;
Pyrenophora species such as, for example, *Pyrenophora teres*;
Ramularia species such as, for example, *Ramularia collocygni*;
Rhynchosporium species such as, for example, *Rhynchosporium secalis*;
Septoria species such as, for example, *Septoria apii*;
Typhula species such as, for example, *Typhula incamata*;
Venturia species such as, for example, *Venturia inaequalis*;

Root and stem diseases caused by, for example,
Corticium species such as, for example, *Corticium graminearum*;
Fusarium species such as, for example, *Fusarium oxysporum*;
Gaeumannomyces species such as, for example, *Gaeumannomyces graminis*;
Rhizoctonia species such as, for example, *Rhizoctonia solani*;
Tapesia species such as, for example, *Tapesia acuformis*;
Thielaviopsis species such as, for example, *Thielaviopsis basicola*;

Ear and panicle diseases (including maize cobs), caused by, for example,
Alternaria species such as, for example, *Alternaria* spp.;
Aspergillus species such as, for example, *Aspergillus flavus*;
Cladosporium species such as, for example, *Cladosporium* spp.;
Claviceps species such as, for example, *Claviceps purpurea*;
Fusarium species such as, for example, *Fusarium culmorum*;
Gibberella species such as, for example, *Gibberella zeae*;
Monographella species such as, for example, *Monographella nivalis*;

Diseases caused by smuts such as, for example,
Sphacelotheca species such as, for example, *Sphacelotheca reiliana*;
Tilletia species such as, for example, *Tilletia caries*;
Urocystis species such as, for example, *Urocystis occulta*;
Ustilago species such as, for example, *Ustilago nuda*;

Fruit rots caused by, for example,
Aspergillus species such as, for example, *Aspergillus flavus*;
Botrytis species such as, for example, *Botrytis cinerea*;
Penicillium species such as, for example, *Penicillium expansum*;
Sclerotinia species such as, for example, *Sclerotinia sclerotiorum*;
Verticilium species such as, for example, *Verticilium alboatrum*;

Seed- and soil-borne rot and wilts, and seedling diseases, caused by, for example,
Fusarium species such as, for example, *Fusarium culmorum*;
Phytophthora species such as, for example, *Phytophthora cactorum*;
Pythium species such as, for example, *Pythium ultimum*;
Rhizoctonia species such as, for example, *Rhizoctonia solani*;
Sclerotium species such as, for example, *Sclerotium rolfsii*;

Cankers, galls and witches' broom disease, caused by, for example,
Nectria species such as, for example, *Nectria galligena*;

Wilts caused by, for example,
Monilinia species such as, for example, *Monilinia laxa*;

Deformations of leaves, flowers and fruits, caused by, for example,
Taphrina species such as, for example, *Taphrina deformans*;

Degenerative diseases of woody species, caused by, for example,
Esca species such as, for example, *Phaemoniella clamydospora*;

Diseases of inflorescences and seeds, caused by, for example,
Botrytis species such as, for example, *Botrytis cinerea*;

Diseases of the plant tubers, caused by, for example,
Rhizoctonia species such as, for example, *Rhizoctonia solani*;

Diseases caused by bacterial pathogens such as, for example,
Xanthomonas species such as, for example, *Xanthomonas campestris* pv. *oryzae*;
Pseudomonas species such as, for example, *Pseudomonas syringae* pv. *lachrymans*;
Erwinia species such as, for example, *Erwinia amylovora*;

The following diseases of soybeans can preferably be controlled:

Fungal diseases on leaves, stems, pods and seeds caused by, for example,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base caused by, for example,
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also have a potent strengthening effect in plants. They are therefore suitable for mobilizing the plants' defences against attack by undesired microorganisms.

Plant-strengthening (resistance-inducing) substances are understood as meaning, in the present context, those substances which are capable of stimulating the defence system of plants in such a way that, when subsequently inoculated with undesired microorganisms, the treated plants display a substantial degree of resistance to these microorganisms.

In the present case, undesired microorganisms are understood as meaning phytopathogenic fungi, bacteria and viruses. Thus, the substances according to the invention can be employed for protecting plants against attack by the above-mentioned pathogens within a certain period of time after the treatment. The period of time within which their protection is effected is generally extended from 1 to 10 days, preferably 1 to 7 days, after the plants have been treated with the active compounds.

The fact that the active compounds, at the concentrations required for the controlling of plant diseases, are well tolerated by plants permits the treatment of aerial plant parts, of vegetative propagation material and seed, and of the soil.

In this context, the active compounds according to the invention can be employed particularly successfully for controlling cereal diseases such as, for example, against *Puccinia* species and of diseases in viticulture, fruit production and vegetable production such as, for example against *Botrytis, Venturia* or *Alternaria* species.

The active compounds according to the invention are also suitable for increasing the yield. Moreover, they display a low degree of toxicity and are well tolerated by plants.

If appropriate, the active compounds according to the invention can also be used in certain concentrations and application rates as herbicides, for influencing plant growth and for controlling animal pests. If appropriate, they can also be employed as intermediates and precursors for the synthesis of further active compounds.

All plants and plant parts can be treated in accordance with the invention. Plants are understood as meaning, in the present context, all plants and plant populations, such as desired and undesired wild plants or crop plants (including naturally occurring crop plants). Crop plants may be plants which can be obtained by conventional breeding and optimization methods or else by biotechnological and genetic engineering methods or by combinations of these methods, including the transgenic plants and including the plant varieties capable or not capable of being protected by Plant Breeders' rights. Plant parts are understood as meaning all aerial and subterranean plants and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention with the active compounds, of the plants and plant parts, is carried out directly or by acting on their environment, habitat, or store by the customary treatment methods, for example by immersion, spraying, vaporizing, fogging, broadcasting, painting on and, in the case of propagation material, in particular in the case of seeds, furthermore by coating with one or more coats.

In the protection of materials, the substances according to the invention can be employed for protecting industrial materials against attack and destruction by undesired microorganisms.

In the present context, industrial materials are understood as meaning non live materials which have been made for use in technology. For example, industrial materials which are to be protected by active compounds according to the invention from microbial modification or destruction can be glues, sizes, paper and board, textiles, leather, timber, paints and plastic articles, cooling lubricants and other materials which are capable of being attacked or destroyed by microorganisms. Parts of production plants, for example cooling-water circuits, which can be adversely affected by the multiplication of microorganisms may also be mentioned within the materials to be protected. Industrial materials which may be mentioned with preference for the purposes of the present invention are glues, sizes, paper and board, leather, timber, paints, cooling lubricants and heat-transfer fluids, especially preferably wood.

Microorganisms which are capable of bringing about a degradation or modification of the industrial materials and which may be mentioned are, for example, bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms of the following genera:

*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*,
*Staphylococcus* such as *Staphylococcus aureus*.

Depending on their respective physical and/or chemical properties, the active compounds can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is, liquid solvents, pressurized liquefied gases and/or solid carriers, optionally with the use of surface-active agents, that is emulsifers and/or dispersants, and/or foam formers. If the extender used is water, it is also possible to employ for example organic solvents as cosolvents.

Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example, to improve the activity spectrum or prevent the development of resistance. In many instances, synergistic effects are obtained, i.e. the activity of the mixture exceeds the activity of the individual components.

Examples of co-components in mixtures are the following compounds:

Fungicides:

1) Nucleic acid synthesis inhibitors: for example benalaxyl, benalaxyl-M, bupirimate, clozylacon, dimethirimol, ethirimol, furalaxyl, hymexazol, mefenoxam, metalaxyl, metalaxyl-M ofurace, oxadixyl, oxolinic acid;

2) Mitosis and cell division inhibitors: for example benomyl, carbendazim, diethofencarb, ethaboxam, fuberidazole, pencycuron, thiabendazole, thiophanate-methyl, zoxamide;

3) Respiration inhibitors (inhibitors of the respiratory chain):
3.1) Inhibitors which act on complex I of the respiratory chain: for example diflumetorim;
3.2) Inhibitors which act on complex II of the respiratory chain: for example boscalid/nicobifen, carboxin, fenfuram, flutolanil, furametpyr, furmecyclox, mepronil, oxycarboxin, penthiopyrad, thifluzamide;
3.3) Inhibitors which act on complex III of the respiratory chain: for example amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) Decouplers: for example dinocap, fluazinam, meptyldinocap;

5) ATP production inhibitors: for example fentin acetate, fentin chloride, fentin hydroxide, silthiofam;

6) Amino acid and protein biosynthesis inhibitors: for example andoprim, blasticidin-S, cyprodinil, kasugamycin, kasugamycin hydrochloride hydrate, mepanipyrim, pyrimethanil;

7) Signal transduction inhibitors: for example fenpiclonil, fludioxonil, quinoxyfen;

8) Lipid and membrane synthesis inhibitors: for example biphenyl, chlozolinate, edifenphos, iodocarb, iprobenfos, iprodione, isoprothiolane, procymidone, propamocarb, propamocarb hydrochloride, pyrazophos, tolclofos-methyl, vinclozolin;

9) Inhibitors of ergosterol biosynthesis: for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) Cell wall synthesis inhibitors: for example benthiavalicarb, dimethomorph, flumorph, iprovalicarb, polyoxins, polyoxorim, validamycin A;

11) Melanin biosynthesis inhibitors: for example carpropamid, diclocymet, fenoxanil, phthalide, pyroquilon, tricyclazole;

12) Resistance inductors: for example acibenzolar-5-methyl, probenazole, tiadinil;

13) Compounds with multi-site activity: for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations such as, for example, calcium polysulphide, thiram, tolylfluanid, zineb, ziram;

14) a compound selected from the following enumeration: N-methyl-(2E)-2-(2-{[6-(3-chloro-2-methylphenoxy)-5-fluoropyrimidin-4-yl]oxy}phenyl)-2-(methoxyimino)acetamide, N-methyl-(2E)-2-{2-[({[(1E)-1-(3-{[(E)-1-fluoro-2-phenylvinyl]oxy}phenyl)ethylidene]amino}oxy)methyl]phenyl}-2-(methoxyimino)acetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2-(4-chlorophenyl)-N-{2-[3-methoxy-4-(prop-2-yn-1-yloxy)phenyl]ethyl}-2-(prop-2-yn-1-yloxy)acetamide, 2,3,5,6-tetrachloro-4-(methylsulphonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts thereof, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo-[1,5-a]pyrimidine-7-amine, 5-chloro-7-(4-methylpiperidin-1-yl)-6-(2,4,6-trifluorophenyl) [1,2,4]triazolo-[1,5-a]pyrimidine, 5-chloro-N-[(1R)-1,2-dimethylpropyl]-6-(2,4,6-trifluorophenyl)[1,2,4]triazolo[1,5-a]-pyrimidine-7-amine, 8-hydroxyquinoline sulphate, benthiazole, bethoxazin, capsimycin, carvone, quinomethionate, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, methasulfocarb, methyl (2-chloro-5-{(E)-N-[(6-methylpyridin-2-yl)methoxy]ethanimidoyl}-benzyl)carbamate, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl 3-(4-chlorophenyl)-3-{[N-(isopropoxycarbonyl)valyl]amino}propanoate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulphonamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-$N^2$-(methylsulphonyl)valinamide, N-{(Z)-[(cyclopropylmethoxy)imino][6-

(difluoromethoxy)-2,3-difluorophenyl]methyl}-2-phenylacetamide, N{2-[3-chloro-5-(trifluoromethyl)pyridin-2-yl]ethyl}-2-(trifluoromethyl)benzamide, natamycin, nickel dimethyl dithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphoric acid and its salts, piperalin, propamocarb fosetylate, propanosine-sodium, proquinazid, pyrrolnitrine, quintozene, tecloftalam, tecnazene, triazoxide, trichlamide, zarilamid.

Bactericides:

Bronopol, dichlorophen, nitrapyrin, nickel dimethyl dithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholine Esterase (AChE) Inhibitors
1.1 Carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
1.2 Organophosphates (for example acephate, azamethiphos, azinphos (-methyl, -ethyl), bromophosethyl, bromfenvinfos (-methyl), butathiofos, cadusafos, carbophenothion, chlorethoxyfos, chlorfenvinphos, chlormephos, chlorpyrifos (-methyl-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)
2. Sodium Channel Modulators/Voltage-Dependent Sodium Channel Blockers
2.1 Pyrethroids (for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, iniprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum))

2.2 Oxadiazines (For Example Indoxacarb)
3. Acetylcholine receptor agonists/antagonists
3.1 Chloronicotinyls/neonicotinoids (for example acetamiprid, clothianidin, dinotefuran, imidacloprid, nitenpyram, nithiazine, thiacloprid, thiamethoxam)
3.2 Nicotine, bensultap, cartap
4. Acetylquoline Receptor Modulators
4.1 Spinosyns (For Example Spinosad)
5. GABA-Controlled Chloride Channel Antagonists
5.1 Cyclodiene organochlorines (for example camphechlor, chlordane, endosulfan, gamma-HCH, HCH, heptachlor, lindane, methoxychlor
5.2 Fiprols (for example acetoprole, ethiprole, fipronil, vaniliprole)
6. Chloride Channel Activators
6.1 Mectins (for example abamectin, avermectin, emamectin, emamectin benzoate, ivermectin, milbemectin, milbemycin)
7. Juvenile Hormone Mimetics
(for example diofenolan, epofenonane, fenoxycarb, hydroprene, kinoprene, methoprene, pyriproxifen, triprene)
8. Ecdysone Agonists/Disruptors
8.1 Diacylhydrazines (for example chromafenozide, halofenozide, methoxyfenozide, tebufenozide)
9. Chitin Biosynthesis Inhibitors
9.1 Benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)
9.2 Buprofezin
9.3 Cyromazine
10. Inhibitors of Oxidative Phosphorylation, ATP Disruptors
10.1 Diafenthiuron
10.2 Organotins (for example azocyclotin, cyhexatin, fenbutatin oxide)
11. Uncouplers of Oxidative Phosphorylation by Interrupting the H-Proton Gradient
11.1 Pyrroles (for example chlorfenapyr)
11.2 Dinitrophenols (for example binapacryl, dinobuton, dinocap, DNOC)
12. Site-I Electron Transport Inhibitors
12.1 METIs (for example fenazaquin, fenpyroximate, pyrimidifen, pyridaben, tebufenpyrad, tolfenpyrad)
12.2 Hydramethylnon
12.3 Dicofol
13. Site-II Electron Transport Inhibitors
13.1 Rotenone
14. Site-III Electron Transport Inhibitors
14.1 Acequinocyl, fluacrypyrim
15. Microbial Disruptors of the Insect Gut Membrane
*Bacillus thuringiensis* strains
16. Fat Biosynthesis Inhibitors
16.1 Tetronic acids (for example spirodiclofen, spiromesifen)
16.2 Tetramic acids [for example 3-(2,5-dimethylphenyl)-8-methoxy-2-oxo-1-azaspiro[4.5]dec-3-en-4-yl ethyl carbonate (also known as: carbonic acid, 3-(2,5-dimethylphenyl)-8-methoxy-2-oxo-1-azaspiro-[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS Reg.-No.: 203313-25-1)]
17. Carboxamides
(for example flonicamid)
18. Octopaminergic Agonists
(for example amitraz)
19. Inhibitors of Magnesium-Stimulated ATPase
(for example propargite)
20. Phthalamides
(for example $N^2$-[1,1-dimethyl-2-(methylsulfonyl)ethyl]-3-iodo-N'-[2-methyl-4-[1,2,2,2-tetrafluoro-1-(trifluoromethyl)ethyl]phenyl]-1,2-benzenedicarboxamide (CAS Reg.-No.: 272451-65-7), flubendiamide)
21. Nereistoxin Analogues
(for example thiocyclam hydrogen oxalate, thiosultap sodium)
22. Biologicals, Hormones or Pheromones
(for example azadirachtin, *Bacillus* spec., *Beauveria* spec., codlemone, *Metarrhizium* spec., *Paecilomyces* spec., thuringiensin, *Verticillium* spec.)
23. Active Compounds with Unknown or Unspecific Mechanisms of Action
23.1 Fumigants (for example aluminium phosphide, methyl bromide, sulfuryl fluoride)
23.2 Selective antifeedants (for example cryolite, flonicamid, pymetrozine)
23.3 Mite growth inhibitors (for example clofentezine, etoxazole, hexythiazox)
23.4 Amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf WO 96/37494, WO 98/25923), and preparations which contain insecticidally active plant extracts, nematodes, fungi or viruses.

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The active compounds can be employed as such, in the form of their formulations or the use forms prepared therefrom, such as ready-to-use solutions, suspensions, wettable powders, pastes, soluble powders, dusts and granules. They are applied in the customary manner, for example by pouring, spraying, atomizing, broadcasting, dusting, foaming, painting on and the like. It is furthermore possible to apply the active compounds by the ultra-low-volume method, or to inject the active compound preparation or the active compound itself into the soil. The seed of the plant can also be treated.

When employing the active compounds according to the invention as fungicides, the application rates can be varied within a substantial range, depending on the type of application. In the treatment of plant parts, the application rates of active compound are generally between 0.1 and 10 000 g/ha, preferably between 10 and 1000 g/ha. For the treatment of seed, the application rates of active compound are generally between 0.001 and 50 g per kilogram of seed, preferably between 0.01 and 10 g per kilogram of seed. For treating the soil, the application rates of active compound are generally between 0.1 and 10 000 g/ha, preferably between 1 and 5000 g/ha.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention. Plant cultivars are understood as meaning plants with new properties ("traits") which have been obtained by conventional cultivation, by mutagenesis or else by recombinant DNA techniques. These may be cultivars, biotypes or genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher harvest yields, better quality and/or a higher nutritional value of the harvested products, better storage stability and/or processability of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes, slugs and snails as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (herein-below referred to as "Bt plants"). Traits which are also particularly emphasized are the increased defence of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulfonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example corn, cotton, soya beans), KnockOut® (for example corn), StarLink® (for example corn), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosates, for example maize, cotton, soya bean), Liberty Link® (tolerance to phosphinothricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

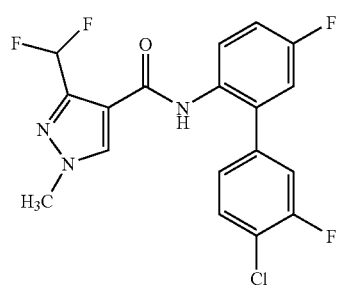 [SMILES: Cn1cc(C(=O)Nc2ccc(F)cc2-c2ccc(Cl)c(F)c2)c(C(F)F)n1]

1.6 ml (18.4 mmol) of oxalyl dichloride and 0.2 ml of dimethylformamide are added to a mixture consisting of 2.96 g (16.8 mmol) of 3-difluoromethyl-1-methyl-1H-pyrazole-4-carboxylic acid in 100 ml of dichloromethane. After 2 hours at room temperature, a solution consisting of 3.83 g (16.0 mmol) of 4'-chloro-5,3'-difluorobiphenyl-2-yl-amine and 2.9 ml (20.8 mmol) in 100 ml of dichloromethane is added. The reaction mixture is stirred for 16 hours at room temperature. For work-up, the reaction mixture is poured into water, and the organic phase is separated, dried over magnesium sulphate and concentrated in vacuo. Column chromatography (petroleum ether/acetone 3:1) yields 5.94 g (93% of theory) of N-(4'-chloro-3',5-difluorobiphenyl-2-yl)-3-(difluoromethyl)-1-methyl-1H-pyrazole-4-carboxamide with a logP (pH 2.3) of 3.05.

The following compounds are obtained analogously to Example 1 and in accordance with the general experimental protocols in the description:
N-(5,3'-difluoro-4'-methylbiphenyl-2-yl)-3-difluoromethyl-1-methyl-1H-pyrazole-4-carboxamide logP (pH 2.3)=3.05
N-(5,3'-difluoro-4'-methylbiphenyl-2-yl)-1-methyl-3-trifluoromethyl-1H-pyrazole-4-carboxamide logP (pH 2.3)=3.27
N-(4'-chloro-5,3'-difluorobiphenyl-2-yl)-1-methyl-3-trifluoromethyl-1H-pyrazole-4-carboxamide logP (pH 2.3)=3.26

Preparation of Starting Materials of the Formula (III)

Example (III-1)

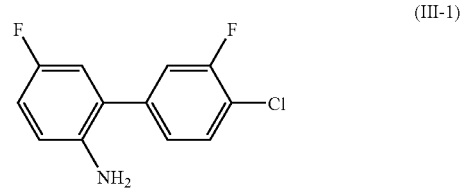 [SMILES: Nc1ccc(F)cc1-c1ccc(Cl)c(F)c1]

Under protective gas atmosphere, a mixture consisting of 30.0 g (0.17 mol) of 4-chloro-3-fluorophenylboronic acid and 29.7 g (0.16 mol) of 2-bromo-4-fluoroaniline in 170 ml of toluene and 17 ml of ethanol is treated with 3.6 g (0.003 mol) of tetrakis(triphenylphosphine)palladium(0) and stirred for 16 h at 80° C. After addition of 200 ml of toluene and 200 ml of water, the organic phase is separated off, dried over magnesium sulphate and concentrated in vacuum. Column chromatography (petroleum ether/acetone 4:1) yields 26.1 g (70% of theory) of 4'-chloro-5,3'-difluorobiphenyl-2-yl-amine with a logP (pH 2.3) of 3.18.

Example (III-2)

Starting from 4-methyl-3-fluorophenylboronic acid and 2-bromo-4-fluoroaniline and proceeding analogously to Example (III-1), the compound 5,3'-difluoro-4'-methylbiphenyl-2-ylamine with a logP (pH 2.3) of 2.94 is obtained.

The logP values stated in the above tables and preparation examples are determined as described in EEC Directive 79/831 Annex V.A8 by means of HPLC (high performance liquid chromatography) on a reversed-phase column (C18). Temperature: 43° C.

The determination is effected in the acidic range at pH 2.3 using 0.1% aqueous phosphoric acid and acetonitrile as eluents; linear gradient from 10% acetonitrile to 90% acetonitrile.

The calibration is effected with unbranched alkan-2-ones (having 3 to 16 carbon atoms) whose logP values are known (determination of the logP values with reference to the retention times by linear interpolation between two successive alkanones).

The lambda-max values were determined with reference to the UV spectra from 200 nm to 400 nm in the maxima of the chromatographic signals.

Use Examples

Example A

| Botrytis test (bean)/protective | |
|---|---|
| Solvent: | 24.5 parts by weight of acetone |
| | 24.5 parts by weight of dimethylacetamide |
| Emulsifier: | 1 part by weight of alkylaryl polyglycol ether |

To prepare an expedient active compound preparation, 1 part by weight of active compound is mixed with the stated amounts of solvent and emulsifier, and the concentrate is diluted to the desired concentration with water.

To test for protective activity, young plants are sprayed with the active compound preparation at the application rate stated. After the spray coating has dried on, 2 small agar blocks which sustain the growth of *Botrytis cinerea* are placed on each leaf. The inoculated plants are placed in a darkened chamber at approximately 20° C. and 100% relative atmospheric humidity.

2 days after the inoculation, the size of the lesions on the leaves is evaluated. 0% means an efficacy which corresponds to that of the control, while an efficacy of 100% means that no disease is observed.

TABLE A

| Botrytis test (bean)/protective | | |
|---|---|---|
| Active compound | Application rate of active compound in ppm | Efficacy in % |
| Disclosed in WO 03/070705 (Ex. 10): | 100 | 52 |

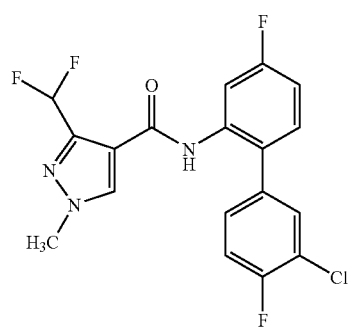

TABLE A-continued

| Botrytis test (bean)/protective | | |
|---|---|---|
| Active compound | Application rate of active compound in ppm | Efficacy in % |
| Disclosed in WO 03/070705 (Ex. 12): | 100 | 87 |

According to the invention: 100 100

Example B

*Pyrenophora teres* Test (Barley)/Protective

To prepare an expedient active compound preparation, 1 part by weight of active compound is mixed with the stated amounts of solvent and emulsifier, and the concentrate is diluted to the desired concentration with water.

To test for protective activity, young plants are sprayed with the active compound preparation at the application rate stated. After the spray coating has dried on, the plants are sprayed with a conidial suspension of *Pyrenophora teres*. The plants remain in an incubation cabinet for 48 hours at 20° C. and 100% relative atmospheric humidity.

The plants are then placed into a greenhouse at a temperature of approximately 20° C. and a relative atmospheric humidity of approximately 80%.

The test is evaluated 8 days after the inoculation. 0% means an efficacy which corresponds to that of the control, while an efficacy of 100% means that no disease is observed.

TABLE B

Pyrenophora teres test (barley)/protective

| Active compound | Application rate of active compound in ppm | Efficacy in % |
|---|---|---|
| Disclosed in WO 03/070705 (Ex. 10): | 1000 | 93 |

[Chemical structure: pyrazole carboxamide with difluoromethyl group, N-methyl pyrazole, connected via amide to biphenyl bearing F, Cl, F substituents]

Solvent: 25 parts by weight of N,N-dimethyl-acetamide
Emulsifier: 0.6 part by weight of alkylaryl polyglycol ether

| Acording to the invention: | 1000 | 100 |
|---|---|---|

[Chemical structure: analogous pyrazole carboxamide with difluoromethyl, N-methyl pyrazole, biphenyl with F, Cl, F substituents]

Solvent: 50 parts by weight of N,N-dimethyl-acetamide
Emulsifier: 1.0 part by weight of alkylaryl polyglycol ether

TABLE C

Erysiphe test (barley)/protective

| Active compound | Application rate of active compound in ppm | Efficacy in % |
|---|---|---|
| Disclosed in WO 03/070705 (Ex. 10): | 1000 | 33 |

[Chemical structure: pyrazole carboxamide with difluoromethyl group, N-methyl pyrazole, connected via amide to biphenyl bearing F, Cl, F substituents]

Solvent: 25 parts by weight of N,N-dimethyl-acetamide
Emulsifier: 0.6 part by weight of alkylaryl polyglycol ether

| Acording to the invention: | 1000 | 78 |
|---|---|---|

[Chemical structure: analogous pyrazole carboxamide with difluoromethyl, N-methyl pyrazole, biphenyl with F, Cl, F substituents]

Solvent: 50 parts by weight of N,N-dimethyl-acetamide
Emulsifier: 1.0 part by weight of alkylaryl polyglycol ether

Example C

*Erysiphe* Test (Barley)/Protective

To prepare an expedient active compound preparation, 1 part by weight of active compound is mixed with the stated amounts of solvent and emulsifier, and the concentrate is diluted to the desired concentration with water.

To test for protective activity, young plants are sprayed with the active compound preparation at the application rate stated.

After the spray coating has dried on, the plants are dusted with spores of *Erysiphe graminis* fsp. *hordei*.

The plants are placed in a greenhouse at a temperature of approximately 20° C. and a relative atmospheric humidity of approximately 80% to favour the development of mildew pustules.

The test is evaluated 7 days after the inoculation. 0% means an efficacy which corresponds to that of the control, while an efficacy of 100% means that no disease is observed.

Example D

*Leptosphaeria nodorum* Test (Wheat)/Protective

To prepare an expedient active compound preparation, 1 part by weight of active compound is mixed with the stated amounts of solvent and emulsifier, and the concentrate is diluted to the desired concentration with water.

To test for protective activity, young plants are sprayed with the active compound preparation at the application rate stated. After the spray coating has dried on, the plants are sprayed with a spore suspension of *Leptosphaeria nodorum*. The plants remain in an incubation cabinet for 48 hours at 20° C. and 100% relative atmospheric humidity.

The plants are then placed into a greenhouse at a temperature of approximately 15° C. and a relative atmospheric humidity of approximately 80%.

The test is evaluated 10 days after the inoculation. 0% means an efficacy which corresponds to that of the control, while an efficacy of 100% means that no disease is observed.

TABLE D

| | Leptosphaeria nodorum test (wheat)/protective | |
|---|---|---|
| Active compound | Application rate of active compound in ppm | Efficacy in % |
| Disclosed in WO 03/070705 (Ex. 10): | 1000 | 0 |

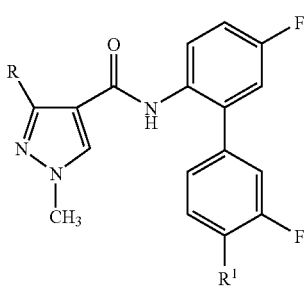

Solvent: 25 parts by weight of N,N-dimethyl-acetamide
Emulsifier: 0.6 part by weight of alkylaryl polyglycol ether

| | | |
|---|---|---|
| Acording to the invention: | 1000 | 84 |

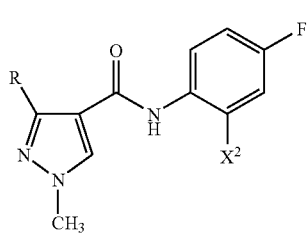

Solvent: 50 parts by weight of N,N-dimethyl-acetamide
Emulsifier: 1.0 part by weight of alkylaryl polyglycol ether

The invention claimed is:

1. A compound of formula (I)

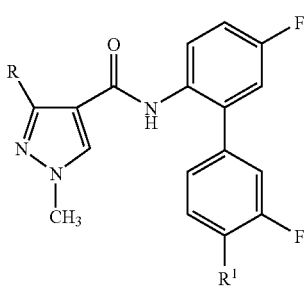

(I)

wherein
R is difluoromethyl or trifluoromethyl, and
$R^1$ is chloro or methyl.

2. The compound of formula (I) according to claim 1, selected from the group consisting of
N-(4'-chloro-3',5-difluorobiphenyl-2-yl)-3-(difluoromethyl)-1-methyl-1H-pyrazole-4-carboxamide,
N-(4'-chloro-3',5-difluorobiphenyl-2-yl)-1-methyl-3-(trifluoromethyl)-1H-pyrazole-4-carboxamide,
N-(3',5-difluoro-4'-methylbiphenyl-2-yl)-1-methyl-3-(difluoromethyl)-1H-pyrazole-4-carboxamide, and
N-(3',5-difluoro-4'-methylbiphenyl-2-yl)-1-methyl-3-(trifluoromethyl)-1H-pyrazole-4-carboxamide.

3. A process for preparation of the compound of formula (I) according to claim 1, comprising reacting a) a compound of formula (II)

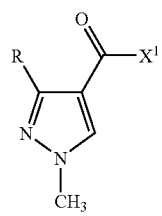

(II)

wherein
R is difluoromethyl or trifluoromethyl, and
$X^1$ is halo,
with a compound of formula (III)

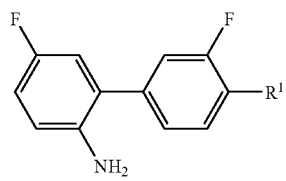

(III)

wherein
$R^1$ is chloro or methyl,
optionally in the presence of an acid binder and optionally in the presence of a diluent, or b) a compound of formula (IV)

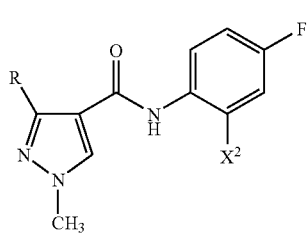

(IV)

wherein
R is difluoromethyl or trifluoromethyl, and
$X^2$ is bromo or iodo with a compound of formula (V)

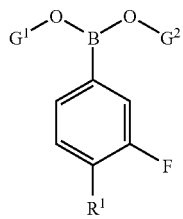

wherein
R¹ is chloro or methyl and
G¹ and G² are in each case hydrogen or together are tetramethylethylene, in the presence of a catalyst, optionally an acid binder and optionally a diluent, or
c) a compound of formula (IV)

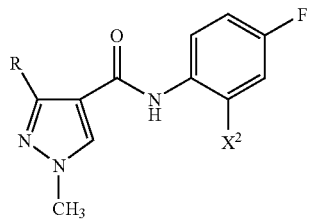

wherein
R is difluoromethyl or trifluoromethyl, and
X² is bromo or iodo
in a first step, with a compound of formula (VI)

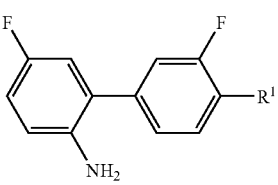

wherein
G³ and G⁴ are in each case alkyl or together are alkanediyl, in the presence of a catalyst, optionally an acid binder and optionally a diluent and, without work-up, in a second step with a compound of formula (VII)

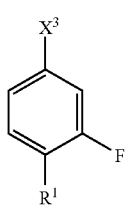

wherein
R¹ is chloro or methyl and
X³ is bromo, iodo or trifluoromethylsulphonyloxy
in the presence of a catalyst, optionally an acid binder and optionally a diluent.

4. A composition for controlling undesired microorganisms, comprising the compound of formula (I) according to claim 1, and an extender, a surface-active substance, or combinations thereof.

5. A method of controlling undesired microorganisms, comprising contacting the compound of formula (I) according to claim 1 with a microorganism or its environment.

6. A process for preparation of a composition for controlling undesired microorganisms, comprising mixing the compound of formula (I) according to claim 1 with an extender or a surface-active substance.

7. An aniline derivative of formula (III)

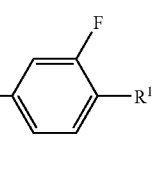

wherein
R¹ is chloro or methyl.

8. The method of claim 5, wherein the undesired microorganisms are on crops.

9. The method of claim 5, wherein the undesired microorganisms are on materials.

10. The compound of formula (I) according to claim 1, which is N-(4'-chloro-3',5-difluorobiphenyl-2-yl)-3-(difluoromethyl)-1-methyl-1H-pyrazole-4-carboxamide.

11. The process of claim 3, wherein the compound of formula (I) is N-(4'-chloro-3',5-difluorobiphenyl-2-yl)-3-(difluoromethyl)-1-methyl-1H-pyrazole-4-carboxamide.

12. The composition of claim 4, wherein the compound of formula (I) is N-(4'-chloro-3',5-difluorobiphenyl-2-yl)-3-(difluoromethyl)-1-methyl-1H-pyrazole-4-carboxamide.

13. The method of claim 5, wherein the compound of formula (I) is N-(4'-chloro-3',5-difluorobiphenyl-2-yl)-3-(difluoromethyl)-1-methyl-1H-pyrazole-4-carboxamide.

14. The process of claim 6, wherein the compound of formula (I) is N-(4'-chloro-3',5-difluorobiphenyl-2-yl)-3-(difluoromethyl)-1-methyl-1H-pyrazole-4-carboxamide.

* * * * *